United States Patent [19]
Honzawa et al.

[11] Patent Number: 5,576,212
[45] Date of Patent: Nov. 19, 1996

[54] OXIDIZING COMPOSITION IN POWDER FORM

[75] Inventors: Katsu Honzawa, Hamamatsu; Seiji Kawaguchi, Ayase; Kazuhiro Atsumi; Fumihiko Shimomura, both of Hamamatsu; Takahiko Ishiguro, Ayase; Hisaya Motojima, Toshima-ku, all of Japan

[73] Assignee: Biosensor Laboratories Co., Ltd., Tokyo, Japan

[21] Appl. No.: 338,740

[22] Filed: Nov. 9, 1994

[30] Foreign Application Priority Data

Nov. 12, 1993 [JP] Japan ................................. 5-283516

[51] Int. Cl.⁶ ................................................. G01N 21/76
[52] U.S. Cl. ............................ 436/8; 436/172; 252/186.3
[58] Field of Search ................................. 436/172, 93, 8; 514/53, 180; 252/700, 186.24, 186.26, 186.42, 186.3, 186.31

[56] References Cited

U.S. PATENT DOCUMENTS

| | | | |
|---|---|---|---|
| 3,671,450 | 6/1972 | Rauhut et al. | 252/186 |
| 3,774,022 | 11/1973 | Dubrow et al. | 252/188.3 X |
| 4,365,018 | 12/1982 | Crutchfield et al. | 430/139 |
| 4,835,142 | 5/1989 | Suzuki. | |

OTHER PUBLICATIONS

Clinical Chemistry, 29/8, pp. 1474–1479 (1983) Weeks, I et al, Acridinium Esters as High–Specific–Activity Labels in Immunoassay.
Hall et al, DE 245 3659 Abstract Only.
Yoshida JP 03284621 Abstract.
Garner–Gray EP 164778 Abstract.

Primary Examiner—Jeffrey Snay
Attorney, Agent, or Firm—Cushman Darby & Cushman, L.L.P.

[57] ABSTRACT

An oxidizing composition in the form of powder for oxidizing a chemiluminescent substance, including an oxidizing agent and a binder.

6 Claims, 2 Drawing Sheets

MEASURING SENSITIVITY OF ACRIDINUM LUMINESCENCE

OXIDIZING COMPOSITION IN POWDER FORM

BACKGROUND OF THE INVENTION

1. Field of the Invention

The present invention relates to an oxidizing composition (or oxidant composition) in the form of powder, which is applicable to a chemiluminescence reaction (or chemical reaction for emitting chemiluminescence) of a chemiluminescent substance (or chemiluminescence-emitting substrate), and to a method of measuring chemiluminescence by using the oxidizing composition. The oxidizing composition and the measurement method according to the present invention are particularly suitable for qualitative or quantitative analysis of a biological substance and/or another minor (or trace) substance.

2. Related Background Art

Chemiluminescence is luminescence as a result of a chemical reaction. A chemiluminescence course or process generally includes a step in which molecules are excited in a chemical reaction to be converted into an excited state via a transition state, and the molecules are then caused to emit light while they are returned to the ground state.

The fluorometry (i.e., analytical method utilizing fluorescence), which is one of typical high-sensitivity analytical methods for measuring substances, requires a light source (or excitation source) such as xenon lamp for exciting fluorescent molecules. Accordingly, in a case where the fluorometry is applied to high-sensitivity analysis, the background level in the measurement is liable to be elevated because of a stray light phenomenon due to the light source and of Raman effect (or Raman light) due to a solvent to be used in the measurement. Further, the background level in this analysis is liable to vary due to fluctuation in the light emitted from the light source. Consequently, when the sensitivity of a detector to be used for the fluorometry is simply enhanced in the fluorometry, the noise level in the measurement is also elevated along with an increase in the signal level.

On the other hand, high-sensitivity analysis on the basis of chemiluminescence (hereinafter called 'chemiluminescence analysis') has been focused in recent years. In the chemiluminescence analysis, since chemiluminescent molecules are excited on the basis of a chemical reaction (or chemical energy), additional light source as an excitation source is not required. Thus, the chemiluminescence analysis has an advantage such that the sensitivity of a detector to be used therefor may be increased without consideration of the above-mentioned effect of a light source on the measurement. In addition, the chemiluminescence analysis also has other advantages such that it has a wide dynamic range, it can use a relatively simple detector, and it takes a relatively short period of time for the measurement (e.g., as described in "Kagaku Kogyo Shiryo", Vol. 22 (No. 4), pp. 111–127 (1987) written by Honda, K), which is hereby incorporated by references.

When an organic compound is used as chemiluminescent molecules, chemiluminescence emission is effected through an oxidation reaction in many cases. In such a case, hydrogen peroxide ($H_2O_2$) is typically used as an oxidizing agent for accelerating the oxidation reaction. For example, when an organic chemiluminescent composition such as luminol derivative or an acridine derivative is used as a chemiluminescent molecules, a basic (or alkaline) hydrogen peroxide is added to such chemiluminescent molecules in order to convert the molecules into an excited state and cause them to emit chemiluminescence (e.g., as described in Imai, K. "SEIBUTSU HAKKO-TO-KAGAKU HAKKO (Bioluminescence and Chemiluminescence)", p.83, published by Hirokawa Publishing Co. Tokyo JAPAN), the disclosure of which is hereby incorporated by references. In addition, an acridinium ester capable of emitting chemiluminescence is used as a high-specific-activity label in immunoassay in Weeks, I., et al.; Clinical Chemistry, Vol.29 (8), pp.1474–1479, (1983), which is hereby incorporated by references.

In recent years, detection method of a trace substance with a higher sensitivity has been expected, and various luminescent molecules or substances having a higher quantum efficiency have been developed (e.g., as described in the "SEIBUTSU HAKKO-TO-KAGAKU HAKKO(Bioluminescence and Chemiluminescence)", p. 79 and p. 103).

However, the operability such as portability or workability in the above-mentioned conventional chemiluminescent systems is poor.

SUMMARY OF THE INVENTION

An object of the present invention is to provide a chemiluminescent reagent having an excellent operability.

Another object of the present invention is to provide a chemiluminescent system which is suitable for high-sensitivity detection of a trace substance.

As a result of earnest study, the present inventors have found that a chemiluminescent system excellent in portability, operability and workability may be provided by utilizing a solidified (i.e., dried) or powdered oxidizing agent in place of a conventional liquid oxidizing agent.

The oxidizing composition according to the present invention is based on the above discovery and comprises an oxidizing agent and a binder.

The oxidizing composition of the present invention may have a particle size of about 1000 μm or smaller.

The oxidizing agent may comprise a peroxide, or may comprise at least one species selected from the group consisting of: peroxides, organic acids, metal complexes, metal salts, transition metal oxides and oxidase.

The peroxide may comprise at least one species selected from the group consisting of: sodium perborate monohydrate, sodium perborate tetrahydrate, perphthalic acid, sodium peroxypyrophosphate, potassium perborate, peroxomonosulfates, peroxodisulfates, sodium persulfate, sodium perchlorate and perbenzoic acid.

The binder may comprise at least one species selected from the group consisting of: polyvinylpyrrolidone, sodium dodecyl sulfate and polysaccharides, or the binder may comprise polyoxyethylene sorbitan monolaurate. The oxidizing composition of the present invention may further comprise a basic substance.

The method for measuring chemiluminescence according to the present invention comprises:

(a) causing a sample labelled with a chemiluminescent substance to react with an oxidizing composition in the form of powder which comprises an oxidizing agent and a binder; and (b) measuring chemiluminescence emitted from the sample labelled with a chemiluminescent substance. The oxidizing composition of the present invention is in the form of powder or bulk solid of particles. Consequently, following beneficial advantages can be provided when using the oxidizing composition of the invention for chemiluminescence analysis.

In the course of adding the oxidizing composition to a solution containing sample labelled with a chemiluminescent substance, the solution slowly permeate through surface of the composition. This results in locally achieving higher concentration of the oxidizing agent and/or the base in the wetted surface with the solution. Thus higher reaction rate, i.e., higher intensity of chemiluminescence, can be achieved in the wetted surface of the composition, preventing the use of higher oxidizing agent concentration liquid solution, that should be avoided in terms of chemical stability.

In addition, since the oxidizing composition according to the present invention has a powder form and is free from a concentration change which is liable to occur in the case of a liquid, the operability (such as handling property and storeability) thereof is excellent. Further, such an oxidizing composition has an advantage in workability such that it may easily be filled into a hollow member such as hollow cylindrical or hollow conic member.

Furthermore, both an oxidizing agent and a base can be included in the composition of the present invention without causing decomposition reaction of the oxidizing agent, because the composition is a 'dry' solid. Consequently, the composition including both an oxidizing agent and a base can be stored for long term without dilution.

The present invention will become more fully understood from the detailed description given hereinbelow and the accompanying drawings which are given by way of illustration only, and thus are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

Figure 1:
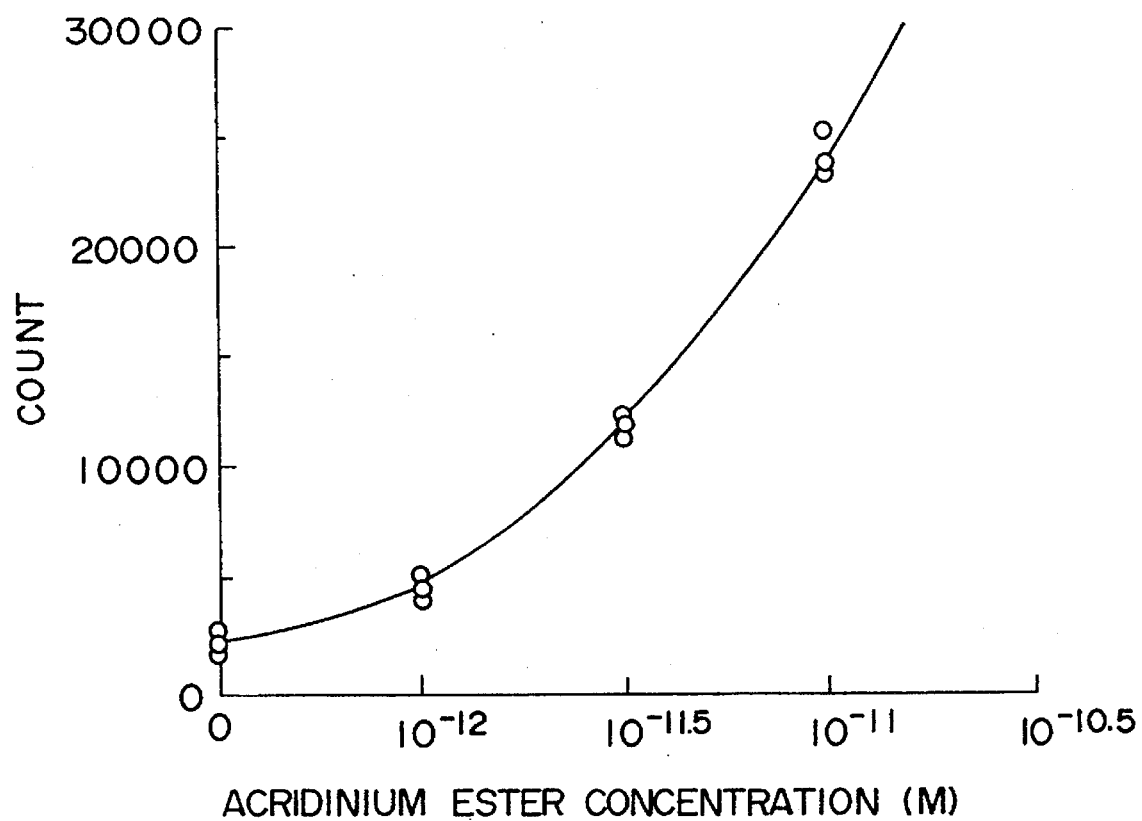
FIG. 1 is a graph showing a relationship of the intensity of chemiluminescence emitted from a chemiluminescent substance with its concentration, which has been obtained in Example 1 appearing hereinafter.

In the following description, "%" and "part(s)" representing a quantitative proportion or ratio are by weight (i.e., "wt. %" and "wt. part(s)") unless otherwise indicated.

(Oxidizing agent)

The type or kind of an oxidizing agent to be usable in the present invention is not particularly limited, as long as it is solid at normal temperature (25°), and it has an effect of oxidizing a chemiluminescent substance (or substrate) described hereinbelow to raise the chemiluminescent substance to an excited state. Specific examples thereof may include: peroxides (such as peracids), metal complexes (such as iron complexes), metallic salts, transition metal oxides, oxidase, etc. These oxidizing agents may be used in combination of two or more species, as desired. Peroxides may preferably be used in view of achieving higher reactivity thereof with the chemiluminescent substance to be described hereinbelow.

Preferred examples of the peroxide may include: inorganic peroxides (e.g., inorganic peracids and their salts) such as perboric acid salts, perchloric acid salts, persulfric acid salts; organic peroxides (e.g., organic peracids and their salts) such as perbenzoic acids; etc. In view of obtaining prompt emission of intense luminescence, a perboric acid salt is particularly preferred.

(Binder)

As a binder constituting the oxidizing composition according to the present invention in combination with the oxidizing agent described above, a water-soluble substance may be used without particular limitation, as long as it is solid at normal temperature (25° C.) and it is not substantially reactive with the above-mentioned oxidizing agent so as not to substantially inhibit the reaction of the chemiluminescent substance with the oxidizing agent described hereinbelow.

In view of easiness in the reaction of the oxidizing composition according to the present invention with the chemiluminescent substance described hereinbelow, the binder may preferably have a water solubility such that 1 (one) gram of the binder may be dissolved in water in an amount of not more than 2 ml (more preferably, not more than 1 ml) at a temperature of 25° C. Such a solubility test may preferably be conducted in accordance with "General Rule 22" of Japanese Pharmacopeia (Tenth Revision).

As a binder, it is possible to use one selected from natural (animal-, vegetable- or microbial-), synthetic or semi-synthetic substances inclusive of water-soluble high-molecular weight substances or low-molecular weight substances (e.g., an excipient or bulking agent for an internal powder medicine). The molecular weight of such substances is not particularly restricted as long as they are soluble in water.

In view of chemical stability and water solubility, it is preferred to use a polysaccharide as the above-mentioned binder. Specific examples of the polysaccharide may include: starch, starch derivatives, cellulose, cellulose derivatives (such as methyl cellulose and carboxymethyl cellulose), hemicellulose (such as agar), dextrin, dextran, etc. In view of water solubility, dextran is particularly preferred. The above-mentioned binders may be used in a combination of two or more species, as desired.

When a peroxide is used as the oxidizing agent, it is preferred to use a binder (such as dextran) which is easily soluble under an acidic condition (at a pH of about 1.5 to 2.0; pH corresponding to acidity of citric acid), in view of the stability of the peroxide during the preparation of powder.

Further, in view of an achieving higher luminescent intensity, polyoxyethylene sorbitan monolaurate (e.g., trade name: "Tween-20", available from Polysciences, Inc.) may preferably be used as the binder.

In the oxidizing composition of the present invention, it is preferred to use about 10–100 parts of a binder with respect to 10 parts of the oxidizing agent.

(Additive)

The oxidizing composition according to the present invention comprises at least the above-mentioned oxidizing agent and binder, but the oxidizing composition may further contain an optional additive such as pH-modifying agent, as desired.

The pH-modifying agent may be used as desired, so as to provide an appropriate pH value for facilitating the reaction or chemiluminescence of the chemiluminescent substance described hereinbelow in combination with the above-mentioned oxidizing agent. For example, in a case where a chemiluminescent substance (such as acridine derivative) capable of emitting intense fluorescence under a basic condition is used, it is preferred to use a basic substance (more preferably, weak basic substance) as a pH-modifying agent. As such a basic substance, it is particularly preferred to use one showing substantially no deliquescence (e.g., a carbonate such as sodium carbonate).

When the pH-modifying agent is used, it is preferred to determine the appropriate amount for achieving higher intensity of luminescence from the chemiluminescent substance. The amount of the pH-modifying agent to be used for such a purpose may preferably be an amount of about 10–100 parts with respect to 10 parts of the oxidizing agent.

(Powder oxidizing composition)

The particle size (or grain size) of the oxidizing composition according to the present invention is not particularly limited, but may preferably be 1000 µm or less, more preferably 350 µm or less (i.e., a particle size capable of passing through a "No. 42 sieve (350 µm)" (Tyler standard sieve, USA), in view of the solubility of the composition in a liquid medium such as water.

(Process for producing oxidizing composition)

The process for preparing the oxidizing composition according to the present invention is not particularly limited. For example, it is possible to prepare a powder product by mixing a solid oxidizing agent with a binder in a liquid (or solution) state under a condition under which the solid oxidizing agent is substantially stable (e.g., under acidic condition, when the oxidizing agent comprises a peroxide), drying the resultant mixture under a relatively milder condition, and then crushing or comminuting the resultant product into bulk solid materials.

In a case where an any additive is added to the oxidizing composition according to the present invention, the additive may be added to the binder together with the oxidizing agent. Alternatively, it is also possible to prepare the above-mentioned powder product (comprising the oxidizing agent and the binder), and then add the additive to the powder product. When a pH-modifying agent such as basic substance is added to the composition, it is preferred to prepare a powder composition by adding the pH-modifying agent in a powder form to a powder product comprising the oxidizing agent and the binder, and mixing it with the powder product (and again crushing or comminuting the resultant product, as desired), in view of easier production of a powder oxidizing composition having good solubility and good stability (e.g., easy production of a powder oxidizing composition capable of providing chemiluminescence with good stability for a long period of time).

(Chemiluminescent substance)

The type or kind of a chemiluminescent substance to be used for a chemiluminescence analysis in combination with the oxidizing composition of the present invention is not particularly limited, as long as it can be oxidized by the above-mentioned oxidizing agent to produce chemiluminescence. Typical examples of such a chemiluminescent substance may include: luminol derivatives such as luminol and isoluminol; dioxetane derivatives; lophine derivatives such as 2,4,5-triphenylimidazole; acridine derivatives such as lucigenin, acridinium salts and acridinium esters; oxalic acid derivatives such as TCPO (bis(2,4,6-trichlorophenyl) oxalate), DNPO (bis(2,4-dinitrophenyl) oxalate); phenanthroline derivatives; siloxene derivatives; indole derivatives; Schiff bases such as N-(isopropylmethylene)-2-anthracenylamine; etc. Among these, it is preferred to use a luminol derivative, an acridine derivative, and/or an indole derivative in view of satisfactory measurement of a trace substance.

(Containment of oxidizing composition)

The oxidizing composition according to the present invention may be contained in a container, as desired. When the composition is contained in a container, it becomes easier to handle the composition. In addition, in such a case, it is easy to preliminary provide the oxidizing composition in a predetermined amount corresponding to the amount of the chemiluminescent substance to be used in combination with the oxidizing composition.

The shape and size of the container to be used for the measurement of chemiluminescence is not particularly limited, as long as the powder oxidizing composition may uniformly be filled or loaded into the container, and the composition may be subjected to a chemiluminescent reaction powder without particular obstruction. In view of efficient measurement of light emitted from the chemiluminescent substance, the internal volume of the container for containing the oxidizing composition may preferably be about 50 µl to 1000 µl, more preferably 100 µl to 300 µl. For easier measurement of chemiluminescence, the amount of the oxidizing composition to be loaded into the container may preferably be about 1 to 50 mg with respect to a container having an internal volume of 100 µl.

As described hereinabove, the oxidizing composition according to the present invention may be used for oxidizing a chemiluminescent substance in known chemiluminescence analysis methods and known assay methods on the basis of chemiluminescence.

Hereinbelow, the present invention will be described in more detail with reference to specific Examples.

EXAMPLE 1

One hundred milligrams (100 mg) of $NaBO_3 \cdot 4H_2O$ as a solid oxidizing agent, and 900 mg of dextran as a binder were added to 400 µl of a 0.3M aqueous citric acid solution to form a mixture in the form of a paste, and the resultant mixture was then dried by heating at 70° C. for 2 hours, and crushed or pulverized into a powder product. To the resultant powder product, $Na_2CO_3$ (pH-modifying agent) in an amount, the volume of which was three times that of the powder product, was added and mixed therewith. Then the resultant mixture was pulverized to provide an oxidizing composition according to the present invention.

By use of the thus obtained oxidizing composition, an acridinium salt of (4-(2-succinimidyloxycarbonylethyl) phenyl-10-methylacridinium-9-arboxylate fluorosulfonate), a chemiluminescent substance, was subjected to a chemiluminescent reaction to produce chemiluminescence. The sensitivity obtained in this measurement is shown in the graph of FIG. 1.

In this chemiluminescent measurement, 4 mg of the above-mentioned oxidizing composition according to the present invention was placed in a cell (volume: 1 ml, made of glass), 150 µl of an aqueous solutions of the above-mentioned acridinium salt each having a concentration as shown in FIG. 1 was added to the oxidizing composition, and the resultant luminescence (wavelength: 250–800 nm) emitted from each of the resultant reaction mixtures (solutions) was measured for 20 seconds by using a luminometer.

EXAMPLE 2

Chemiluminescent was measured in the same manner as in Example 1, except that the weight ratio of the above-mentioned $NaBO_3 \cdot 4H_2O$ (solid oxidizing agent) and $Na_2CO_3$ (pH-modifying agent) ($NaBO_3 \cdot 4H_2O/Na_2CO_3$) was changed to 1/99, 1/70, 1/49, 1/30, 1/9, 3/7, 1/1, 7/3 and 9/1 ($NaBO_3 \cdot 4H_2O+Na_2CO_3=3$ mg).

Figure 2:
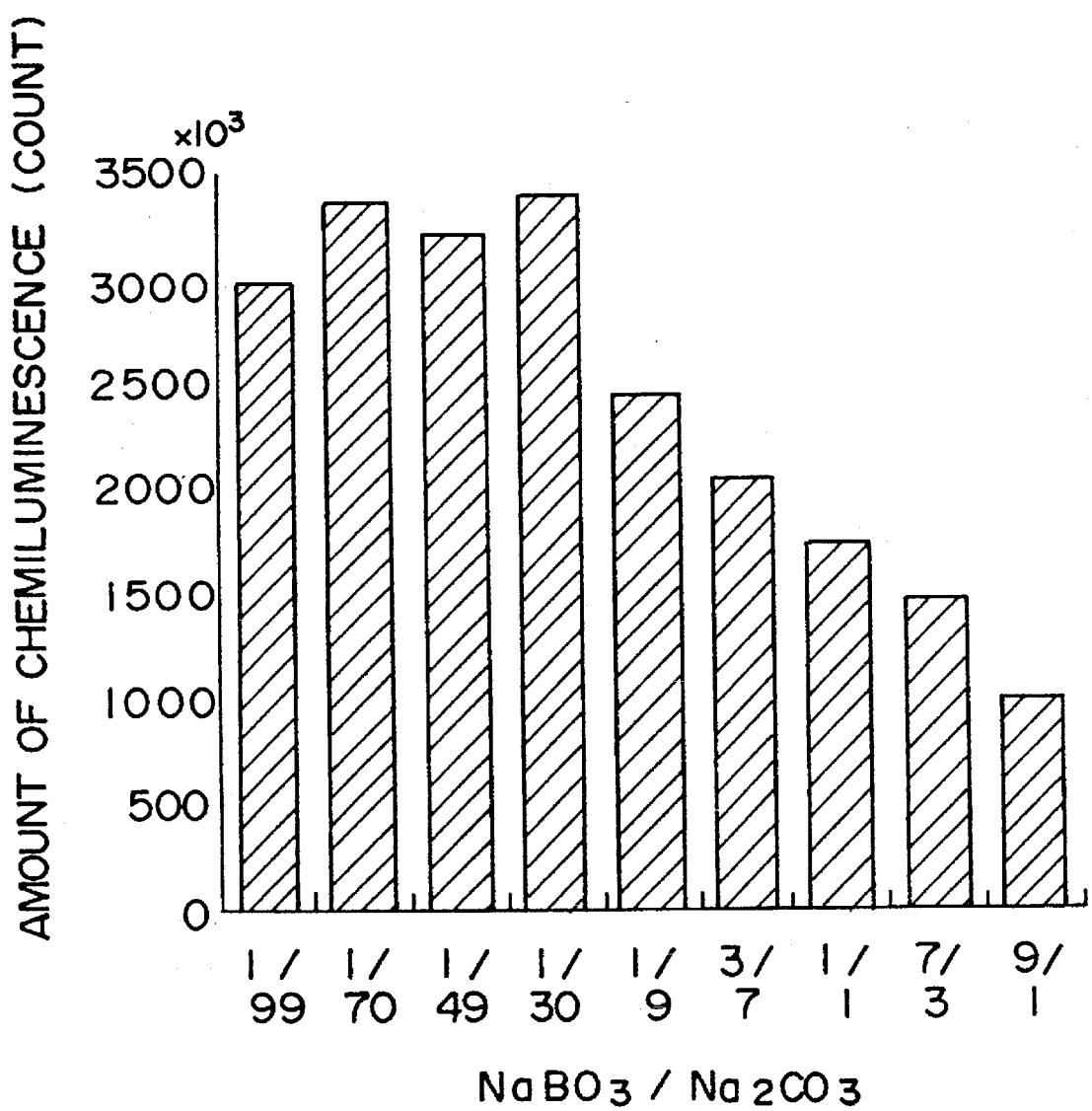
FIG. 2 is a graph showing a relationship of the intensity of chemiluminescence with $NaBO_3 \cdot 4H_2O/Na_2CO_3$ ratio of an oxidizing composition, which has been obtained in Example 2 appearing hereinafter.

The results of the measurement are shown in the graph of FIG. 2.

As shown in FIG. 2, in view of the quantity (or intensity) of chemiluminescence, the ratio of ($NaBO_3 \cdot 4H_2O/Na_2CO_3$) was preferred in the range of 1/100 to 1/10 (particularly, in the range of 1/70 to 1/30).

EXAMPLE 3

(Stability of powder oxidizing composition)

Each of three milligrams (3 mg) of the oxidizing composition according to the present invention prepared in Example 1 (comprising the solid oxidizing agent, binder and pH-modifying agent) and 25 μl of a basic aqueous solution of hydrogen peroxide ($H_2O_2$ concentration: 0.1%, NaOH concentration: 1N) as a liquid oxidizing agent was separately added to 150 μl of the aqueous acridinium salt solution (concentration: $1 \times 10^{-11}$M) used in Example 1 and allowed to react therewith, and the quantity of chemiluminescence emitted from each the reaction mixtures was measured in the same manner as in Example 1.

Each of the above-mentioned oxidizing agent and liquid oxidizing agent was placed in a separate glass test tube and the resultant test tube was formed into a sealed tube, and then stored for 2 months at 25° C.

Each of the powder and liquid oxidizing agents after the storage was added to the above-mentioned aqueous acridinium salt solution to cause a chemiluminescent reaction, and the chemiluminescence emitted from each of the reaction mixtures was measured in the same manner as in Example 1. As a result, substantially no deterioration was observed in either of the oxidizing agents (loss of the quantity of luminescence was at most about 2–3% as compared with that provided by the oxidizing compositions before the storage).

As described hereinabove, according to the present invention, there is provided a oxidizing composition for chemiluminescence characterized by comprising at least a solid oxidizing agent and a binder.

Since the oxidizing composition according to the present invention is in the form of powder and the volume thereof is relatively small (for example, about 1/10 to 1/100 as compared with the volume of an oxidizing agent in the form of a solution), the volume of the entire chemiluminescent system may be reduced as compared with that of a conventional chemiluminescent system, whereby the efficiency of chemiluminescence measurement may be improved and high-sensitivity detection may be achieved. Accordingly, the oxidizing composition according to the present invention may suitably be used in qualitative and quantitative analysis of a trace substance such as biological substance, etc.

In addition, when the oxidizing composition according to the present invention is used, it is possible to miniaturize a device or apparatus for measuring chemiluminescent, on the basis of a decrease in the volume of the entire chemiluminescent system as described above.

Moreover, since the oxidizing composition according to the present invention is in the form of powder and is not substantially susceptible to evaporation of a component constituting the composition unlike a liquid composition, its handling property (easiness in handling and storeability, etc.) is good. In addition, the composition according to the present invention may be easily loaded into a hollow member such as chip.

From the invention thus described, it will be obvious that the invention may be varied in many ways. Such variations are not to be regarded as a departure from the spirit and scope of the invention, and all such modifications as would be obvious to one skilled in the art are intended to be included within the scope of the following claims.

The basic Japanese Application No.283516/1993 filed on Nov. 12, 1993 is hereby incorporated by reference.

What is claimed is:

1. An oxidizing agent composition in dry particulate form comprising effective amounts of:

(a) sodium perborate tetrahydrate, (b) sodium carbonate, (c) citric acid, and (d) binder, wherein the ratio of the sodium perborate tetrahydrate to the sodium carbonate contained in said composition is in the range of about 1:1 to about 1:30 by weight, and wherein the particle size of said oxidizing agent composition is less than about 1,000 μm.

2. An oxidizing agent composition according to claim 1, wherein the binder is selected from the group consisting of dextran, hydroxypropylmethylcellulose, hydroxypropyl cellulose and polyoxyethylene sorbitan monolaurate.

3. An oxidizing agent composition according to claim 1, wherein the weight ratio of the sodium perborate tetrahydrate to the sodium carbonate is about 1:1.

4. An oxidizing agent composition in dry particulate form comprising:

(a) about 2.5% weight of sodium perborate tetrahydrate, (b) about 74.5% weight of sodium carbonate, (c) about 22.5% weight of dextran, and (d) about 0.5% weight of anhydrous citric acid, wherein the particle size of said oxidizing agent composition is less than about 1,000 μm.

5. An oxidizing agent composition in dry particulate form consisting essentially of:

(a) sodium perborate tetrahydrate;

(b) sodium carbonate;

(c) anhydrous citric acid; and (d) a binder selected from the group consisting of dextran, hydroxypropylmethylcellulose, hydoxypropyl cellulose and polyoxyethylene sorbitan monolaurate;

wherein the ratio of the sodium perborate tetrahydrate to the sodium carbonate contained in said composition is in the range of about 1:1 to about 1:30 by weight, and wherein the particle size of said oxidizing agent composition is less than about 1,000 μm.

6. An oxidizing agent composition in dry particulate form consisting essentially of:

(a) sodium perborate tetrahydrate;

(b) sodium carbonate;

(c) anhydrous citric acid; and
(d) a binder selected from the group consisting of dextran, hydroxypropylmethylcellulose, hydroxypropyl cellulose and polyoxyethylene sorbitan monolaurate, wherein the ratio of the sodium perborate tetrahydrate to the sodium carbonate contained in said composition is in the range of about 1:1 to about 1:30 by weight, and wherein the particle size of said oxidizing agent composition is less than about 1,000 μm, said oxidizing agent composition being a product of the process comprising the steps of:

(i) adding the sodium perborate tetrahydrate and the binder into an aqueous solution of the anhydrous citric acid to obtain a paste mixture;
(ii) drying the paste mixture by heating to form a dry solid mixture;
(iii) crushing or pulverizing the dry solid mixture to obtain a powder mixture;
(iv) adding and mixing the sodium carbonate to the powder mixture, and pulverizing to obtain the oxidizing agent composition.

* * * * *